(12) United States Patent
Haase et al.

(10) Patent No.: US 9,903,817 B1
(45) Date of Patent: Feb. 27, 2018

(54) DISSOLVED GAS SENSOR AND SYSTEM

(71) Applicant: The United State of America, as represented by the Secretary of the Department of the Interior, Washington, DC (US)

(72) Inventors: Karl B. Haase, Herndon, VA (US); Ward E. Sanford, Herndon, VA (US)

(*) Notice: Subject to any disclaimer, the term of this patent is extended or adjusted under 35 U.S.C. 154(b) by 0 days.

(21) Appl. No.: 15/407,095

(22) Filed: Jan. 16, 2017

(51) Int. Cl.
 *G01N 21/61* (2006.01)
 *B01D 19/00* (2006.01)
 *G01N 33/00* (2006.01)

(52) U.S. Cl.
 CPC ......... *G01N 21/61* (2013.01); *B01D 19/0031* (2013.01); *G01N 33/004* (2013.01); *G01N 2201/02* (2013.01)

(58) Field of Classification Search
 CPC ........ G01N 21/35; G01N 21/64; G01N 21/61; G01N 33/004; G01N 2201/02; B01D 19/0031
 See application file for complete search history.

(56) References Cited

U.S. PATENT DOCUMENTS

| | | | | |
|---|---|---|---|---|
| 4,376,681 A * | 3/1983 | Inoue | ..... | G01N 27/38 204/415 |
| 5,121,627 A | 6/1992 | D'Aoust | | |
| 6,037,592 A | 3/2000 | Sunshine et al. | | |
| 7,434,446 B2 | 10/2008 | Johnson et al. | | |
| 2003/0036052 A1* | 2/2003 | Delwiche | ..... | C12Q 1/001 435/4 |
| 2013/0217140 A1 | 8/2013 | Fietzek | | |

OTHER PUBLICATIONS

Bastviken, David, et al. "Technical Note: Cost-efficient approaches to measure carbon dioxide (CO 2) fluxes and concentrations in terrestrial and aquatic environments using mini loggers." Biogeosciences 12.12 (2015) 3849-3859.
Fietzek, Peer, et al. "In situ Quality Assessment of a Novel Underwater p CO2 Sensor Based on Membrane Equilibration and NDIR Spectrometry." Journal of Atmospheric and Oceanic Technology 31.1 (2014): 181-196.
Johnson, Mark S., et al. "Direct and continuous measurement of dissolved carbon dioxide in freshwater aquatic systems—method and applications." Ecohydrology 3.1 (2010): 68-78.
Ohkubo, Shinjiro. "Utility of silicone filter for diffusive model CO 2 sensors in field experiments." Tellus B 65 (2013).

* cited by examiner

*Primary Examiner* — David Porta
*Assistant Examiner* — Faye Boosalis
(74) *Attorney, Agent, or Firm* — Jill Welytok; James Mitchell

(57) ABSTRACT

The dissolved gas sensor system includes a dissolved gas sensor partially located within a housing and partially extending through the housing lid. The sensor is created by affixing a selectively permeable membrane to a dissolved gas transducer with a waterproof polymer. This forms a membrane cavity between the membrane, polymer, and transducer. The membrane cavity allows the transducer to detect whatever gas or gases can pass through the selectively permeable membrane. These readings pass to a controller located within the housing body that can receive and process data, and store the data in a removable data storage for later retrieval by a user. The controller can also regulate overall power consumption of the system to increase the operating life of the system.

19 Claims, 2 Drawing Sheets

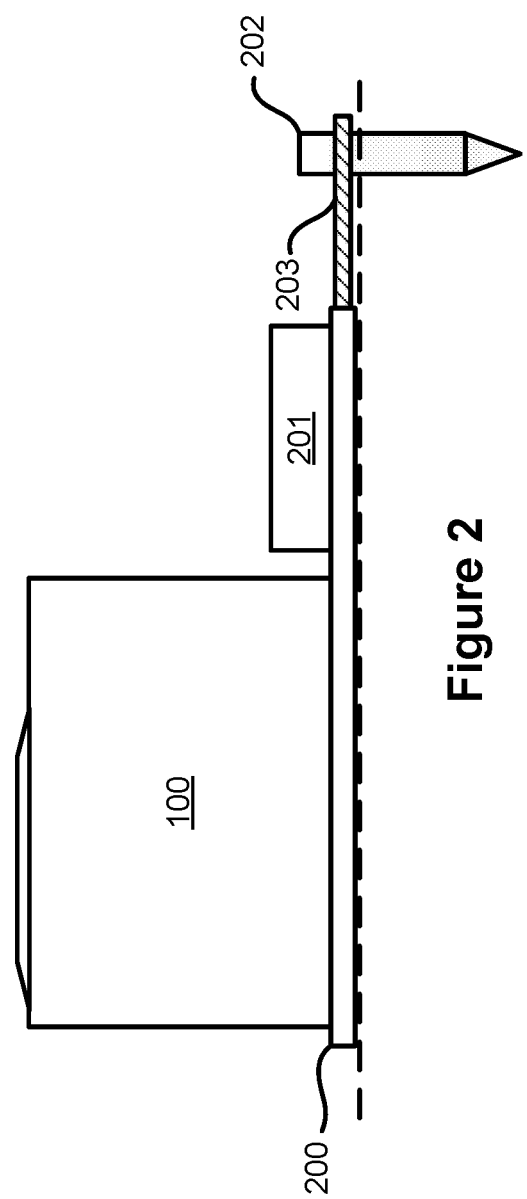

DISSOLVED GAS SENSOR AND SYSTEM

STATEMENT REGARDING FEDERALLY SPONSORED RESEARCH OR DEVELOPMENT

The invention described herein was made by an employee of the United States Government and may be manufactured and used by the Government of the United States of America for governmental purposes without the payment of any royalties thereon or therefore.

FIELD OF INVENTION

This invention relates to the field of gas sensors and more specifically to a dissolved carbon dioxide sensor.

BACKGROUND OF THE INVENTION

Monitoring the levels of dissolved gasses in waterways and the atmosphere allows scientists to evaluate waterway acidification, oxygenation, and pollution, climate change, and other biological and meteorological conditions. In the past, scientists placed sensors in waterways or in open atmosphere to continuously monitor dissolved gas levels. Membranes that were selectively permeable to the gas under study covered the sensors to protect them from fouling, allowing the gas to diffuse into a cavity for detection by the sensor. Cables connected the sensors to power and data logging units to supply power and record sensed gas levels.

The required physical connection to a central data logger makes distribution of such sensors limited, increasing the costs to cover a large area. Because the sensors attach to a central power source, the sensor runtime is also limited, especially in remote areas which require a battery-based power source. Furthermore, the exposure and visibility of the cables and power and data logging units renders the entire system vulnerable to damage, vandalism, or theft. On a smaller scale, membranes attach over the sensor using bolted, machined frames, which increase the sensor unit size and cost, and often lead to mechanical failure of the sensor unit.

There is an unmet need in the art for a self-contained dissolved gas sensor system.

There is a further unmet need in the art for a dissolved gas sensor system capable of membrane attachment without the use of mechanical frames.

BRIEF SUMMARY OF THE INVENTION

The present invention is a dissolved gas sensor system. The system includes a housing having an interconnected housing body and housing lid. A dissolved gas sensor is partially located within the housing and partially extends through the housing lid. The dissolved gas sensor includes a selectively permeable membrane affixed to a dissolved gas transducer with a waterproof polymer. This forms a membrane cavity between the selectively permeable membrane, waterproof polymer, and dissolved gas transducer. The membrane cavity allows the dissolved gas transducer to detect whatever gas or gases can pass through the selectively permeable membrane. These readings pass to a controller located within the housing body. The controller's processor is connected to the dissolved gas sensor and to a power supply. The controller's data logger is connected to the dissolved gas sensor and to the processor, while the controller's power circuit is connected to the power supply. Using these components, the controller can receive and process data, and store the data in a removable data storage. The controller can also regulate overall power consumption of the system.

BRIEF DESCRIPTION OF SEVERAL VIEWS OF THE DRAWING(S)

FIG. 2 illustrates a side view of an exemplary embodiment of the dissolved gas measurement system mounted to a base.

TERMS OF ART

Figure 1:
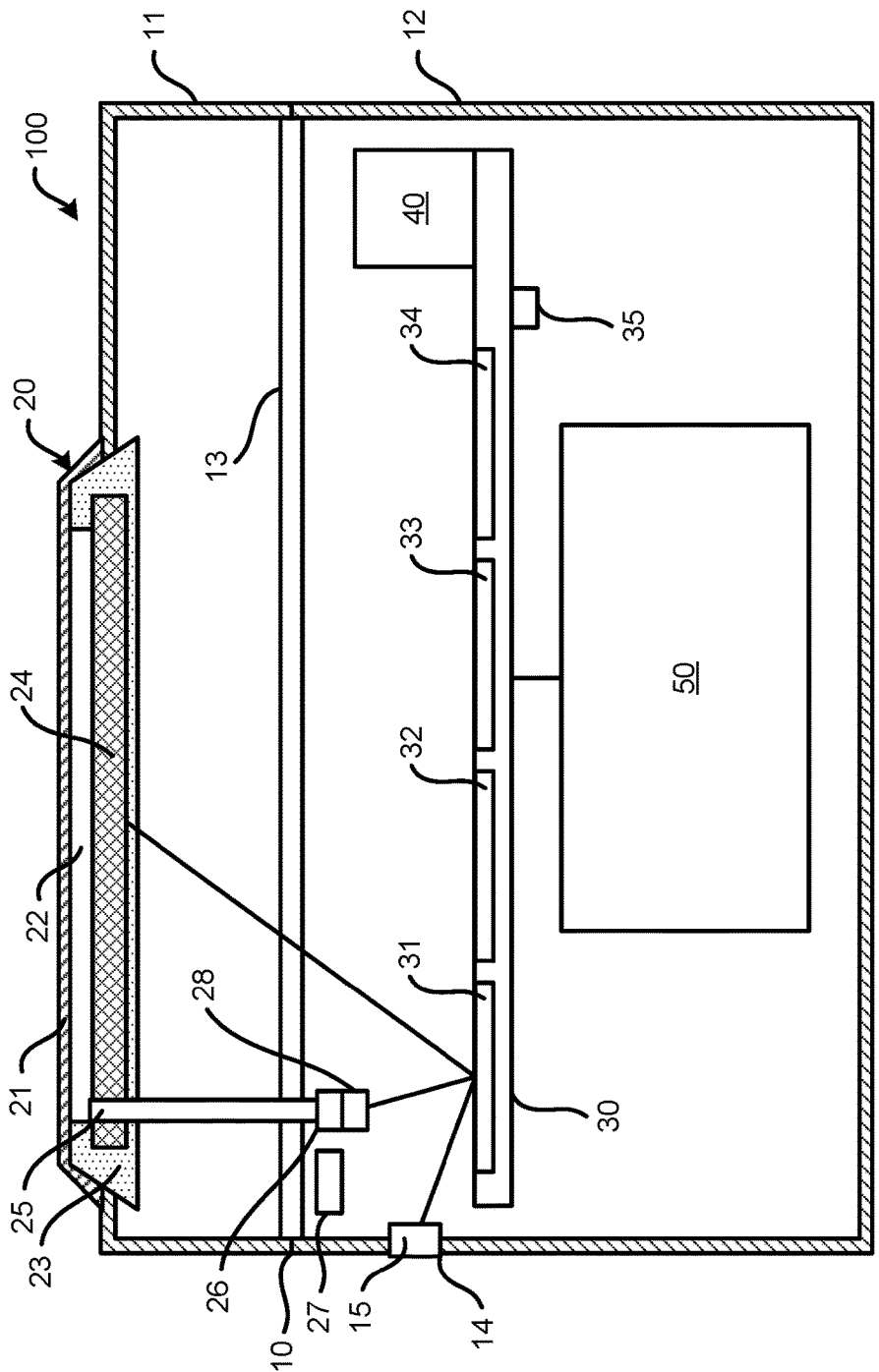
FIG. 1 illustrates a cross-sectional view of an exemplary embodiment of a dissolved gas measurement system.

As used herein, the term "data logger" refers to a device that records data over time.

As used herein, the term "dissolved gas transducer" refers to a device capable of measuring the amount of a specific gas or set of gases dissolved in a solution.

As used herein, the term "processor" refers to any code segment, circuitry or computer system, or other apparatus capable of performing a logical, mathematical, or functional operation, and/or transforming the type, state, value, or condition of actual or modeled data.

As used herein, the term "selectively permeable membrane" refers to a porous membrane which allows passage of a preselected substance or substances while blocking all other substances.

DETAILED DESCRIPTION OF THE INVENTION

FIG. 1 illustrates a cross-sectional view of an exemplary embodiment of dissolved gas measurement system 100. A housing 10 encases part of a dissolved gas sensor 20, along with a controller 30, a removable data storage 40, and optionally, a power supply 50, sealing these components from potential water damage and allowing a user to submerge the entire system 100 if necessary. A remaining portion of dissolved gas sensor 20 protrudes from a housing lid 11. Because housing 10 is sealed, a user must open housing 10 to remove and replace data storage 40 and power supply 50.

Housing 10 is made from a waterproof material such as a metal, a polymer, or a combination thereof. Housing lid 11 moveably connects to a housing body 12, allowing a user to open housing 10 if necessary. The seam between housing lid 11 and housing body 12 is watertight due to a housing seal 13. Housing seal 13 is a flexible, waterproof polymeric or elastomeric material. In the exemplary embodiment, housing seal 13 is a polymer foam ring coated with silicone grease. Optionally, at least one housing port 14 extends through housing 10 to allow the use of at least one additional external sensor 15. Such external sensors 15 may include, but are not limited to, a radiation sensor, such as a photosynthetically active radiation sensor, or a pressure sensor, such as a water pressure sensor or barometer. External sensors 15 may be used to detect external conditions, such as sunlight reception, sensor depth, or water flow. External sensors 15 connect to controller 30 to receive power and to transmit data.

Dissolved gas sensor 20 includes a selectively permeable membrane 21 covering a membrane cavity 22 and sealed with a waterproof polymer 23 to a dissolved gas transducer 24 and to housing lid 11. A calibration tube 25 extends from membrane cavity 22 to a calibration port 26, which may be covered by a removable port cap 27 or connected to a pressure transducer 28.

Selectively permeable membrane 21 is a porous, waterproof polymer membrane. In the exemplary embodiment, selectively permeable membrane 21 is a silicone membrane permeable to carbon dioxide. Other embodiments of selectively permeable membrane 21 may be permeable to other dissolved gasses, such as, but not limited to oxygen, or may be formed from other materials, such as, but not limited to polytetrafluoroethylene. Membrane cavity 22 is sized to accommodate dissolved gas transducer 24, which forms its bottom dimension. The top dimension of membrane cavity 22 is formed by selectively permeable membrane 21, while the side dimension is formed by waterproof polymer 23. Membrane cavity 22 minimizes the quantity of whatever gas or gasses need to pass through selectively permeable membrane 21 for dissolved gas transducer 24 to detect a change in gas concentration.

Waterproof polymer 23 is also impermeable to the gas or gasses measured by dissolved gas transducer 24 to ensure accurate measurement. Furthermore, waterproof polymer 23 does not contain or release any gasses that may interfere with readings made by dissolved gas transducer 24. In the exemplary embodiment, waterproof polymer 23 is a polyurethane cement. In other embodiments, waterproof polymer 23 may be, but is not limited to, epoxy cement or butyl rubber cement. Waterproof polymer 23 interconnects and forms a waterproof seal between selectively permeable membrane 21, dissolved gas transducer 24, and housing lid 11. Dissolved gas transducer 24 measures levels of whatever gas or gasses enter membrane cavity 22 through selectively permeable membrane 21. In the exemplary embodiment, dissolved gas transducer 24 is a non-dispersive infrared transducer for measuring carbon dioxide. Other embodiments may use different dissolved gas transducers 24 for different gasses, such as an ultraviolet flux transducer for measuring oxygen or an infrared transducer for measuring methane. Dissolved gas transducer 24 is connected to controller 30 to receive power and to process and store data.

Calibration tube 25 provides direct access to membrane cavity 22 via calibration port 26. This allows a user to calibrate dissolved gas transducer 24 by opening housing 10 and directly flushing membrane cavity 22 with a calibration gas, instead of merely placing the entire system 100 in an environment filled with calibration gas. Not only does this eliminate the lead time for the gas to cross selectively permeable membrane 21, it also reduces the volume of calibration gas required to calibrate dissolved gas transducer 24. In the exemplary embodiment, dissolved gas transducer 24 is calibrated at 0, 200, 1,000, and 25,000 ppm of the gas under study. After calibration, a user may close off calibration port 26 with removable port cap 27 or connect calibration port 26 to pressure transducer 28. Embodiments utilizing pressure transducer 28 connect pressure transducer 28 to controller 30 to receive power and to transmit data.

Controller 30 includes a processor 31 with a data logger 32 and a power circuit 33, a clock 34, and a temperature sensor 35. Processor 31 is operatively connected to all sensors and to removable data storage 40 and power supply 50. Data logger 32 receives data from all sensors and stores the data in removable data storage 40. Power circuit 33 regulates power consumption for system 100 using clock 34. When system 100 is in a sleep mode, system 100 can consume 20-100 times less power than when system 100 is measuring and recording data, allowing extended data gathering using power supply 50. Further power savings may be attained by programming controller 30 to sleep and conserve power between measurement intervals. Clock 34 also provides a timestamp for any collected data.

Removable data storage 40 is a non-volatile data storage device such as, but not limited to, an SD memory card or a USB flash drive. In the exemplary embodiment, power supply 50 is a 7- to 17-volt power source. In the exemplary embodiment, power supply 50 is a battery pack located inside of housing 10. In other embodiments, power supply 50 may be a solar panel or panels located outside of housing 10 and connected to power circuit 33 through housing 10. This embodiment of system 100 may be used for above-water applications.

When powered on, system 100 enters a warmup mode and warms up dissolved gas transducer 24 for a user selected period of time. After warm up, dissolved gas transducer 24 enters the measurement phase and controller 30 collects data such as, but not limited to, a raw dissolved gas transmittance signal from dissolved gas transducer 24, estimated dissolved gas concentration data, error checking information from dissolved gas transducer 24, a time and date from clock 34, a power level from power supply 50, and/or a temperature signal, at user-defined intervals, from temperature sensor 35. In the exemplary embodiment, dissolved gas transducer 24 collects data at a frequency of 0.5 Hz. Controller 30 saves collected data to removable data storage 40. The raw dissolved gas transmittance signal from dissolved gas transducer 24 may be used in later post processing for final results.

After a user-specified number of samples are recorded to removable data storage 40, system 100 enters sleep mode. The dissolved gas transducer 24 is powered down, and controller 30 suspends processing for user-specified intervals to minimize energy consumption. Every interval, controller 30 wakes, checks the status of clock 34, then determines whether to return to sleep or enter warmup mode for another set of measurements. If system 100 encounters a detectable error, system 100 will reset itself in an attempt to return to a proper mode of measurement operations.

After system 100 has collected a full sequence of data, a user may retrieve system 100 and remove data storage 40. The user may then transfer the data to an external workstation. This external workflow can correct the data for measured or estimated total dissolved gas pressure, barometric pressure variations, water interference with dissolved gas transducer 24, and temperature effects.

FIG. 2 illustrates a side view of an exemplary embodiment of dissolved gas measurement system 100 mounted to base 200. Base 200 has sufficient mass, in the form of base weight 201, to keep system 100 submerged. In certain embodiments, base weight 201 is integral to base 200; that is, base 200 itself has sufficient mass to keep system 100 submerged. In the exemplary embodiment, base 200 is further connected to at least one base anchor 202 by at least one base connector 203 to ensure that system 100 remains in place despite any water currents affecting system 100. Base anchor 202 may be a pipe, stake, or any other anchor known in the art that can be embedded in the ground or a waterway bed to prevent system 100 from being displaced by water currents or any other environmental forces. Base connector 203 may be a cable, chain, rope, or any other connector known in the art. Other embodiments may use environmental features or debris to keep base 200 from moving.

It will be understood that many additional changes in the details, materials, procedures and arrangement of parts, which have been herein described and illustrated to explain the nature of the invention, may be made by those skilled in the art within the principle and scope of the invention as expressed in the appended claims. Moreover, the terms "about," "substantially" or "approximately" as used herein may be applied to modify any quantitative representation that could permissibly vary without resulting in a change in the basic function to which it is related.

It should be further understood that the drawings are not necessarily to scale; instead, emphasis has been placed upon illustrating the principles of the invention.

What is claimed is:

1. A dissolved gas sensor apparatus, comprised of:
 a selectively permeable membrane;
 a dissolved gas transducer;
 a waterproof polymer encapsulated around said dissolved gas transducer and affixing said selectively permeable membrane to said dissolved gas transducer; and
 a membrane cavity formed between said selectively permeable membrane, said waterproof polymer, and encapsulated portions of said dissolved gas transducer; whereby the transducer is embedded in the polymer.

2. The apparatus of claim 1, wherein said selectively permeable membrane is a polymer membrane selected from the group consisting of: polytetrafluoroethylene and silicone.

3. The apparatus of claim 1, wherein said selectively permeable membrane is permeable to at least one gas of interest selected from the group consisting of carbon dioxide, methane, and oxygen.

4. The apparatus of claim 3, wherein said waterproof polymer is impermeable to said gas of interest.

5. The apparatus of claim 1, wherein said waterproof polymer is selected from the group consisting of: polyurethane cement, epoxy cement, and butyl rubber cement.

6. The apparatus of claim 1, wherein said dissolved gas transducer is selected from the group consisting of: ultraviolet flux transducers and infrared transducers.

7. The apparatus of claim 1, wherein said dissolved gas transducer is a non-dispersive infrared transducer.

8. The apparatus of claim 1, further including a calibration tube extending between said membrane cavity and a calibration port.

9. The apparatus of claim 8, wherein said calibration port is capped by a removable port cap.

10. The apparatus of claim 8, wherein said calibration port is connected to a pressure transducer.

11. A dissolved gas sensor system, comprised of:
 a dissolved gas sensor, comprising:
  a selectively permeable membrane,
  a dissolved gas transducer,
  a waterproof polymer encapsulated around said dissolved gas transducer and affixing said selectively permeable membrane to said dissolved gas transducer, and
  a membrane cavity formed between said selectively permeable membrane, said waterproof polymer, and unencapsulated portions of said dissolved gas transducer;
 a housing comprising a housing lid connected to a housing body, wherein at least part of said dissolved gas sensor extends from within said housing and through said housing lid; and
 a controller located within said housing body, wherein said controller comprises:
  a processor connected to said dissolved gas sensor, to a removable data storage, and to a power supply,
  a data logger connected to said dissolved gas sensor and to said removable data storage,
  a power circuit connected to said power supply.

12. The system of claim 11, wherein said controller further includes a clock connected to said processor and said power circuit.

13. The system of claim 11, wherein said system further includes a flexible, waterproof housing seal located between said housing lid and said housing body.

14. The system of claim 11, wherein said system further includes a housing port extending through said housing body and an external sensor extending through said housing port.

15. The system of claim 14, wherein said external sensor is selected from the group consisting of: radiation sensors and pressure sensors.

16. The system of claim 11, wherein said power supply is at least one solar panel located external to said housing.

17. The system of claim 11, wherein said power supply is at least one battery located internal to said housing.

18. The system of claim 11, wherein said system further includes a base connected to said housing, wherein said base includes a base weight having sufficient mass to submerge said system.

19. The system of claim 18, wherein said base further includes at least one base anchor connected to said base by a base connector.

* * * * *